United States Patent [19]

Grundei

[11] Patent Number: 4,600,546

[45] Date of Patent: Jul. 15, 1986

[54] PROCESS FOR THE PRODUCTION OF AN IMPLANT AS A BONE SUBSTITUTE

[75] Inventor: Hans Grundei, Lübeck, Fed. Rep. of Germany

[73] Assignee: S+G Implants GmbH, Lubeck, Fed. Rep. of Germany

[21] Appl. No.: 721,498

[22] Filed: Apr. 9, 1985

Related U.S. Application Data

[63] Continuation-in-part of Ser. No. 508,068, Jun. 24, 1983, abandoned.

[30] Foreign Application Priority Data

Jun. 28, 1982 [DE] Fed. Rep. of Germany ....... 3224265

[51] Int. Cl.$^4$ .................. B29C 33/38; C04B 33/32
[52] U.S. Cl. ..................... 264/59; 164/34; 164/35; 264/221; 264/DIG. 44
[58] Field of Search ......... 264/59, 221, 317, DIG. 44; 164/34, 35, 45; 106/38.25; 501/81, 82; 502/507

[56] References Cited

U.S. PATENT DOCUMENTS 3,266,915 8/1966 Faulkner ..................... 164/34
3,608,051 9/1971 Scott ........................ 264/DIG. 44

*Primary Examiner*—James Lowe
*Attorney, Agent, or Firm*—Balogh, Osann, Kramer, Dvorak, Genova & Traub

[57] ABSTRACT

This invention relates to a process for the production of an implant of metal or plastics material having an open-celled structure as a bone substitute. The process uses a connectively open-celled pattern material having a spatial grid or lattice network structure, the cells or pores of the material being defined or formed by very fine thin interconnected threads or cords. The thin threads are coated by a wax-water emulsion which is combustible and vaporizable. A stabilization of the coating may be performed by spraying-on of a hardening and vaporizable synthetic material lacquer, which is deposited on the wax coating. A core material is introduced into the residual hollow spaces of the pattern, which is consolidated by heat, the pattern material being burnt and vaporized while doing so, together with the adhering material and the lacquer without leaving behind any residues, so that the cavities formed in the core may be filled with the implant material and the core material is finally removed.

3 Claims, No Drawings

PROCESS FOR THE PRODUCTION OF AN IMPLANT AS A BONE SUBSTITUTE

This application is a continuation-in-part of application Ser. No. 508,068, filed on June 24, 1983 now abandoned.

BACKGROUND OF THE INVENTION

The present invention relates to a process for the production of an implant as a bone substitute, in which use is made of a pattern of a material which is connectively open-celled throughout, the cells of which are filled with a core material of ceramic matrix composition, whereupon the material of the pattern is removed by firing the core material, the implant material being cast into the resultant cavities of the core and the core material finally being removed.

For producing a morphologically stable implant of metal or acid-proof plastics material as bone replacement having a connectively open cellular structure throughout, the procedure adopted according to a prior proposal consisted in that the interconnected cells of a sponge acting as an implant pattern, and consisting of a natural or plastics material, were filled with a ceramic matrix composition, the pattern material of which was removed from the core by application of heat whilst simultaneously solidifying the core. The implant material was then cast into the cavities remaining in the core and, after cooling or solidification respectively, the core material was dissolved by means of acids and removed by being blown out by sand-blasting to clean the core.

Conventional methods disclose the use of a plastic foam pattern material having connected pores which are limited by wall partitions or surfaces. If such pores are filled with liquid ceramic embedding mass, which is later burned into a rigid ceramic body, the following problem would result: parts of the burned-out foam pattern material remain adhered to the inner surfaces of the pores or cells and cannot be removed. The inventor has carried out many tests and experiments in an attempt to discover the source of this problem. He found out that adhering parts or residues of the burned-out foam pattern material disposed at the inner surfaces of the pores would eventually become attached to the metal of the bone implant to be produced. Such residues attached to the metal implant may cause later infections in the human body, as well as cancerous tumors and the like.

In attempting to resolve this problem, the inventor tried to make the limitations of the pores or cells of the foam pattern material as small as possible. He has found a plastic foam pattern material in which the limitations of the pores are very small, and the limitations consisting only of very fine or thin threads being reticulated to form a spatial grid or lattice network structure. Such thin threads naturally have to be reinforced by wax, for example, a water emulsion of wax can be applied on the threads at ambient temperature.

The use of water emulsion of wax as reinforcement coating on the threads substantially eliminates the aforementioned problem in the art. During the burning of the ceramic core, the water emulsion evaporates, producing a wrap or cover of evaporated water which escapes. Thereby the adhering of residues of foam pattern material to the inner surfaces of the ceramic core, and in turn to the metal implant, is substantially eliminated.

It was further discovered that the walls of the open-celled foam pattern material acting as a pattern, being expandable material in particular may be too thin under certain circumstances, so that the cavities remaining in the core after extraction of the pattern material may possible not be filled completely with the implant material of metal or plastics material, since its viscosity is too high with respect to the partially too small widths of the cavities.

It is an object of the invention to provide a process wherein the cavities remaining in the core material after removal of the pattern material from the core may be kept so large as to ensure the unobjectionable inflow of fluid metals or acid-proof plastics materials.

SUMMARY OF THE INVENTION

To achieve these and other objects in accordance with the invention, in the process hereinabove set forth, and prior to placing the core material in the pattern, the surfaces of the parts of the pattern forming the cells are provided with a coating which is removed together with the pattern material during the firing of the core material subsequently to be inserted.

As a pattern material having a connectively open-celled or reticulated web structure, the following plastic material, natural or synthetic, may be used:

A plastic foam material having an open-celled or pored web structure and formed as a spatial grid or lattice network. The cells or pores of such material are defined or formed by very fine thin interconnectecd threads or cords.

Liquified wax may be applied as a coating to the pattern material. The wax forming the coating may also be emulsified in water at only a slightly raised temperature (or ambient temperature), advantageously at say 20° to 30° C., and applied on the pattern sections forming cells by spraying or immersion, so that the wax is deposited thereupon by separation or vaporization of the water on the surfaces or threads delimiting the cells this will increase or thicken the surfaces or walls or webs of the cells or pores.

The threads of the form pattern material are coated by wax in such a way that the diameter of the resulting pores is equal or corresponds to the diameter of the pores of the natural bone to be replaced by the implant.

It is preferable that the threads be coated by a wax-water emulsion at ambient temperature so that evaporation of the water would leave the wax in the form of a dry coating on the threads of the open-celled pattern material.

As explained further below, since the dry coating of wax is loose, it is preferred that a further coating of a plastic resin lacquer be applied on top of the wax coating.

According to another embodiment of the invention, a plastics material lacquer is applied on the coating for stabilization thereof. Lacquers are preferentially utilised which do not leave any residues behind upon firing the core material and thereby removing the pattern material, e.g. such as acrylic lacquer.

The interconnected threads or reticulated web surfaces delimiting the connectively open-pored cells are reinforced by the method in accordance with the invention, in such degree that after the remanent interconnected cells have been filled with the core material and the pattern material has been removed, without leaving any adhering residues, cavities are left which may in any event be filled with fluid metal or acid-proof plastics material. A ceramic matrix composition, such as that utilised for the production of casting moulds, may be used for example as a core material.

The use of the wax-water emulsion for coating of the pattern material threads is critical in preventing the adherence of pattern material residues to the inner surfaces of the ceramic core and in turn, the metal implant. The water of the wax-water emulsion will be evaporated during the burning of the ceramic core, to produce a wrap (or cover) of evaporated water which prevents the adhering of residues to the inner surfaces of the ceramic core.

After the fluid or flowing core material is placed in the cavities, a consolidation of the core is performed by firing, whereby the pattern material as well as the wax and lacquer are removed by being burnt and vaporized without leaving behind any adhering residues, so that the enlarged cavities in the core then allow of casting in metal or acid-proof plastics material. The core material is subsequently removed by dissolution by means of acids, e.g. hydrofluoric acid, whereupon a cleaning operation is performed on the cavities of the implant of connectively open-celled structure throughout, by means of sand blasting or blowing out.

The size (i.e., diameter) of the pores or cavities of the implant should be equal or correspond to the size (i.e., diameter) of the pores of the natural bone to be replaced by the implant.

In conclusion, it is also pointed out that although wax may well be a particularly appropriate coating substance, other materials may also be utilised instead of wax. Plastics materials are primarily envisaged for this purpose.

I claim:

1. In a process for production of an implant for replacing a natural bone, the process being of the type comprising using a pattern of connectively open-celled material, filling the cells of said material with a core material of ceramic matrix composition, removing the pattern material by firing the core material so that cavities remain in the core thus produced, casting the implant material into the cavities of the core, and finally removing the core material, the improvement which comprises using a pattern material having a open-celled web structure and formed as a spatial grid or lattice network, the cells of the pattern material being defined and formed by delicate interconnected threads, prior to placing the core material in the pattern material, coating the threads or walls of the cells with a wax emulsified in water at a temperature of 20°–40° C. so that the diameter of the coated threads corresponds to the diameter of cells of the natural bone replaced by the implant, applying said wax coating as an emulsion on all surfaces of the threads or walls of the cells of the pattern material, so that evaporation of the the water, by surrounding temperature, leaves the wax deposited as a dry coating on the threads or cell walls of the pattern material reinforcing and increasing the surfaces of the threads or cell walls of the pattern material, and following the filling of the cells of the pattern material with the core material, removing said coating together with the pattern material during the firing of the core material.

2. An improved process according to claim 1, further comprises applying a plastics material lacquer over said coating for stabilization thereof.

3. An improved process according to claim 1, wherein said coating of emulsified wax is applied to the threads or walls of the cells by immersion.

* * * * *